(12) United States Patent
Qajar et al.

(10) Patent No.: US 9,274,040 B2
(45) Date of Patent: Mar. 1, 2016

(54) PROCESS FOR CHARACTERIZATION OF MICRO AND MESO POROUS MATERIALS

(71) Applicant: The Penn State Research Foundation, University Park, PA (US)

(72) Inventors: Ali Qajar, State College, PA (US); Ramakrishnan Rajagopalan, State College, PA (US); Henry C. Foley, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 256 days.

(21) Appl. No.: 14/202,569

(22) Filed: Mar. 10, 2014

(65) Prior Publication Data

US 2015/0000377 A1     Jan. 1, 2015

Related U.S. Application Data

(60) Provisional application No. 61/841,464, filed on Jul. 1, 2013.

(51) Int. Cl.
*G01N 15/08* (2006.01)
(52) U.S. Cl.
CPC .................................. *G01N 15/088* (2013.01)
(58) Field of Classification Search
CPC ... G01N 15/0826; G01N 15/088; G91N 3/12; E21B 49/00; G01L 27/00
USPC .................................. 73/38, 37, 152.05, 1.57
See application file for complete search history.

(56) References Cited

U.S. PATENT DOCUMENTS 4,972,730 A * 11/1990 Camp ................ G01N 15/0893
                                                                            73/865.5
7,421,885 B2 * 9/2008 Kitzhoffer ......... G01N 15/0893
                                                                              702/43

OTHER PUBLICATIONS

Grabica et al, Adsorption properties of ordered mesoporous silicas synthesized in the presence of block copolymer pluronic F127 under microwave irradiation, Adsorption, Oct. 2010, vol. 16, Issue 4 pp. 385-396.*

* cited by examiner

*Primary Examiner* — Lisa Caputo
*Assistant Examiner* — Nigel Plumb
(74) *Attorney, Agent, or Firm* — Dinsmore & Shohl LLP

(57) ABSTRACT

A process for characterizing micro, meso, and/or macro porous materials is provided. The process includes providing a volumetric and/or gravimetric adsorption system, the adsorption system having an adsorption chamber and a probe gas at a first temperature. In addition, a porous material to be characterized is provided and placed within the adsorption chamber. Thereafter, a porosimetry run is conducted on the porous material. The porosimetry run includes: (a) selecting an uptake target value; (b) selecting a target interval bounding the target uptake target value; (c) adjusting pressure within the adsorption chamber in order for the porous sample to reach the target uptake value; (d) adjusting pressure within the adsorption chamber until the pressure within the adsorption chamber is within the target interval for a predetermined amount of time; and (e) repeating steps (a)-(d) until the porosimetry run is complete.

20 Claims, 9 Drawing Sheets

PROCESS FOR CHARACTERIZATION OF MICRO AND MESO POROUS MATERIALS

CROSS-REFERENCE TO RELATED APPLICATIONS

This application claims priority of U.S. Provisional Patent Application Ser. No. 61/841,464 filed Jul. 1, 2013, which is incorporated herein in its entirety by reference.

FIELD OF THE INVENTION

The present invention relates in general to a process for characterization of micro, meso, and macro pores, and in particular to a process that uses pressure uptake manipulation for characterization of micro, meso, and macro pores in a porous material.

BACKGROUND OF THE INVENTION

The advancement of reaction and separation technologies requires the ongoing development of porous materials. For example, the development of porous carbons having high porosity has led to their wide use in industrial applications such as catalysis, capacitor electrodes, adsorptive gas separations and gas storage. In addition, in applications such as optics and shape selective catalysis, where the ordering of a porous material is important, aluminosilicate structures are of special interest.

It is appreciated that engineering new porous materials requires knowledge on the textural properties and their relationship to the performance of the material. Furthermore, it is known that pore volume and surface area are properties indicative of the capacity of a given porous material. Pore size distribution (PSD) is also useful since it is sensitive to pore size, geometry and pore connectivity.

Porosimetry, i.e. the characterization of porous materials using gas adsorption, is a well-known technique. Typically, pore size distribution of a sample is determined by dosing gas into the pores. The measured gas uptake is used to interpret the frequency of pore size at a corresponding pressure, along with micro, meso and total pore volume, plus surface area of the sample. Porosimetry with $N_2$ and Ar is conducted at cryogenic temperatures to keep the adsorption pressures below atmospheric. This eases some instrumental requirements as high pressures are not required, however, such low temperatures slow down adsorption rates inside microporous materials such that true equilibrium of the gas uptake is not achieved. With this in mind $CO_2$ adsorption measurements at 273 K have been used for micropore characterization. Thus, as of today, the most prevalent method to characterize the micro, meso and macro pores of a material is to use $N_2$ adsorption isotherm for meso and macro pores and then $CO_2$ adsorption for the micropores. The pore size distribution can then be determined from an adsorption isotherm using appropriate models.

It is appreciated that different molecules can give different information regarding a given sample pore structure and pore connectivity due to a molecule's inherent size and polarizability, and its interactions with pore size and surface chemistry of the adsorbent. Moreover, characterization models usually assume pore walls to be smooth with no chemical heterogeneity. However, in most cases this is not an accurate assumption and can thus result in errors in the pore size distribution calculations. In addition, the use of two different probe molecules can introduce different degrees of uncertainty for micro and mesopore regions.

Regarding adsorption techniques, adsorption measurements are mostly conducted using volumetric or gravimetric instruments. Volumetric instruments typically have a relatively simple design and operate based on pressure changes during gas adsorption on the adsorbent in a known confined volume. Also, adsorption analysis using volumetric instruments is typically employed for adsorption measurements using light gases near room temperature.

Gravimetric instruments measure gas uptake using magnetic micro-balances. This method is less accurate for small quantities of uptake of light gases like $H_2$. However, gravimetric instruments use an uptake measurement sensor that is separated from a pressure transmitter and thus pressure can be altered independently while collecting adsorption data.

Not being bound by theory, adsorption of a gas on an adsorbent in a confined volume reduces the gas pressure. Therefore, gas can be injected at controlled flow rates into the adsorption chamber in order to maintain a constant pressure. It addition, the effect of pressure changes on gas uptake rates depends on the rates of surface adsorption and molecular diffusion dynamics for a given the adsorbent-adsorbate system.

A kinetic approach to an adsorption process can be treated as a collection of elementary steps where each step is a linear function of the adsorption driving force (e.g. pressure of more chemical potential). In the alternative, pseudo-first and pseudo-second order kinetic models are used to describe adsorption dynamics since they can fit on a large variety of adsorption processes. They are special cases of a more general expression, Langmuirian adsorption kinetics. Taking the kinetics approach to the Langmuir isotherm the following expressions can be written as:

$$r_a = k_a P(\theta_e - \theta) \tag{1a}$$

$$r_d = k_d \theta \tag{1b}$$

where $r_a$ and $r_d$ are the adsorption and desorption rates, respectively, $k_a$ and $k_d$ are the adsorption and desorption rate constants, respectively, $\theta$ is the surface coverage, $\theta_e$, is the equilibrium coverage at each measurement condition, and P is the gas pressure. By subtracting these two terms the net rate of adsorption can be obtained as:

$$d\theta/dt = k_a P(\theta_e - \theta) - k_d \theta \tag{2}$$

While the rate constants, $k_a$ and $k_d$ are typically functions of temperature, but not pressure, when the adsorption measurements are made under isothermal and isobaric conditions, they remain constant. Hence, the adsorption rate is a first order function of the concentration (chemical potential) gradient.

Aside from pressure and temperature effects, the nature of adsorbent porosity plays the dominant role in determining gas adsorption dynamics. In particular, gas uptake is associated with micropore filling, monolayer completion in micropores, and capillary condensation inside mesopores. In addition, when adsorption equilibrium data are collected at moderate to high resolution, i.e. during small changes in pressure, the adsorption dynamics can be expressed as a function of pressure.

Conventional adsorption instruments dose the adsorbate gas into the system and then allow no disturbances until the local equilibrium (or pseudo-equilibrium) point is reached. However, such a condition can and often does take a very long time to reach when using nitrogen at 77K. As such, an improved process for characterizing micro and mesoporous materials would be desirable.

SUMMARY OF THE INVENTION

A process for characterizing micro, meso, and/or macro porous materials is provided. The process includes providing a volumetric and/or gravimetric adsorption system, the adsorption system having an adsorption chamber and a probe gas at a first temperature. In addition, a porous material to be characterized is provided and placed within the adsorption chamber. Thereafter, a porosimetry run is conducted on the porous material. The porosimetry run includes: (a) selecting an uptake target value; (b) selecting a target interval bounding the uptake target value; (c) adjusting pressure within the adsorption chamber in order for the porous sample to reach the uptake target value; (d) adjusting pressure within the adsorption chamber until the pressure within the adsorption chamber is within the target interval for a predetermined amount of time; and (e) repeating steps (a)-(d) until the porosimetry run is complete.

In some instances, the process further includes determining if a predetermined pressure has been reached within the adsorption chamber after step (d). If the predetermined pressure has been reached, the probe gas is cooled from the first temperature to a predetermined lower second temperature. In addition, steps (a)-(d) are repeated using the probe gas at the second temperature until the porosimetry run is complete. Finally, the completed porosimetry run is operable to obtain one complete set of pore size distribution data ranging from micropores to mesopores to macropores.

The probe gas may or may not be methyl chloride (MeCl). Also, the adsorption system can have a cooler or chiller that is operable to cool the probe gas from the first temperature to the second temperature. In the event that the probe gas is cooled from the first temperature to the second temperature, the cooling can occur isobarically.

The porosimetry run can be a single porosimetry run that has a pressure range between $10^{-7}$ to 760 Torr. In the alternative, the porosimetry run can be a single run with pressures between 0.001 to 760 Torr. Alternatively, the porosimetry run can be a single run between 0.01 to 760 Torr.

The target interval is less than or equal to +/−20% of the target gas uptake value, preferably less than or equal to +/−15% of the target gas uptake value, and more preferably less than or equal to +/−10% of the target gas uptake value.

The adsorption system has a probe gas inlet valve and a probe gas outlet valve that adjusts the pressure within the adsorption chamber by configuring the probe gas inlet valve or the probe gas outlet valve to be in an open position. Also, the probe gas inlet valve and the probe gas outlet valve are both in the closed position when the pressure within the adsorption chamber is within the target interval. In the event that the pressure within the adsorption chamber drops below the target interval, the probe gas inlet valve is placed in an open position. In the alternative, when the pressure in the adsorption chamber rises above the target interval, the probe gas outlet valve is placed in the open position.

DETAILED DESCRIPTION OF THE INVENTION

The present invention provides a process for characterization of micro- and meso-porous materials by using an accelerated method that affords achieving equilibrium target uptake within a much shorter time span than heretofore known processes. As such, the present invention has use as a porosimetry technique for characterizing porous materials.

The process includes placing a porous material in a volumetric and/or gravimetric gas adsorption system and pressure of an uptake is manipulated such that the time required for equilibrium of gas uptake at each adsorption data point is reduced. In gravimetric gas adsorption systems, gas pressure of an adsorbate gas such as $N_2$, Ar, $CO_2$, MeCl and the like is controlled using gas inlet and outlet valves. In volumetric gas adsorption systems, a piston-cylinder arrangement can be used to manipulate gas pressure.

Similar to heretofore known techniques, a sample is placed in or loaded into a sealable sample holder, which is connected to a chamber with gas inlet and gas outlet valves. A certain amount of uptake gas is provided into the sample holder (dosed or dosing) and the system is held under isothermal conditions for a predefined period of time. A current gas uptake is chosen or selected as a target uptake and a pressure control algorithm is used to damp gas uptake changes as fast or quick as possible with gas pressure and sample weight used as equilibrium condition indicators.

The inventive process can be applied to current prior art instruments through a set of simple modifications. In particular, no hardware attachment is required and changes are limited to the pressure control program software for gravimetric instruments. For volumetric systems, a piston-cylinder compartment is added to the instrument along with changes in the adsorption control software. It is appreciated that pressure changes are indicative of gas uptake in volumetric systems and thus the pressure control system cannot arbitrarily dose gas while the system is under non-equilibrium condition. Therefore, the piston-cylinder compartment with a known volume and a sealed moving part is used to manipulate gas pressure while the amount or quantity of gas in the sample holder is held constant.

Figure 2:
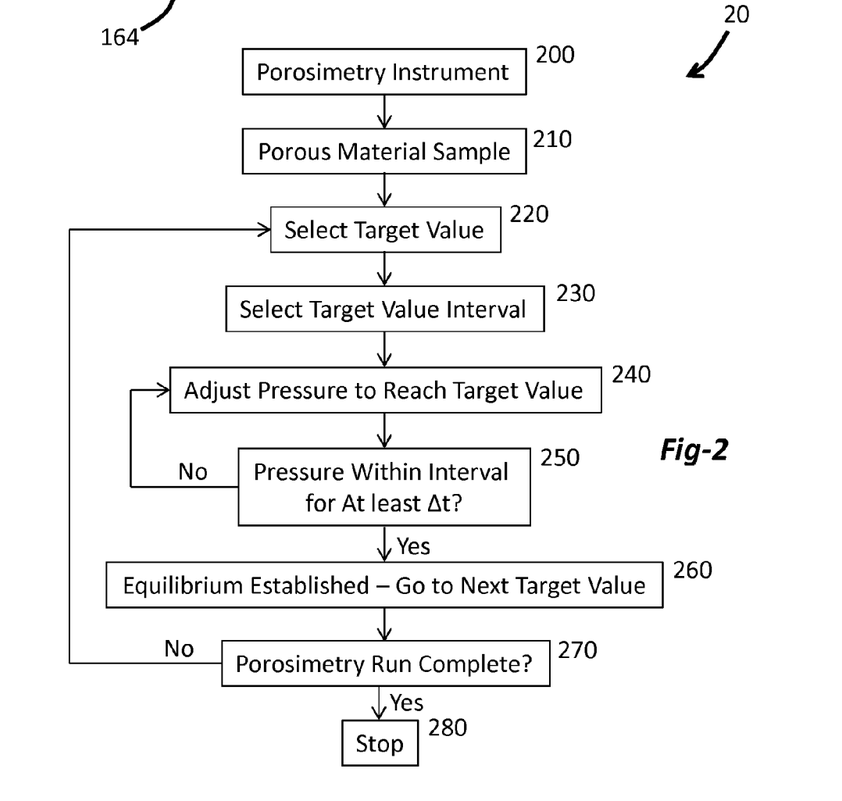
FIG. 2 is a flowchart illustrating a process according to an embodiment of the present invention.

Referring back to Equation 2 above and the expression of the dynamics in the neighborhood of any adsorption equilibrium point, an increase in pressure directly increases the net adsorption rate and vice versa. As such, the Langmuirian rate model is useful in simulating adsorption dynamics in the neighborhood of an equilibrium point. For example, FIG. 2 illustrates a simulated adsorption response to an arbitrary step change in pressure. Clearly, the rise time, i.e. the time in which adsorption uptake reaches a certain target value, depends on the pressure of the gas. Therefore, one can increase the rate of adsorption by elevating the initial pressure above the target pressure. Then once an acceptable rise in the gas uptake is gained, the pressure can then be reduced accordingly to equilibrate around to a current local equilibrium point.

In principle, even aggressive changes in pressure can be tolerated since any rapid uptake resulting in adsorption is necessarily followed by rapid desorption near that given pressure. However, in practice for most adsorbents, such simple dynamics may not be obtained. For example appearance of hysteresis loops can be assigned to capillary condensation at $P/P_0 > 0.4$ or cavitation effect in the relative pressure range of 0.4 to 0.5. This will limit the rate of desorption and thus limits the rate of attainment of equilibrium at that pressure. As such, the gas uptake rate is moderated, after the initial rise, and, accordingly, the pressure not reduced to a level lower than that of the local equilibrium point being sought. It should be appreciated that using such an approach to accelerate the overall rate of attainment of equilibrium at each pressure so as to reduce the total time necessary to collect the isotherm requires robust control.

Figure 1:
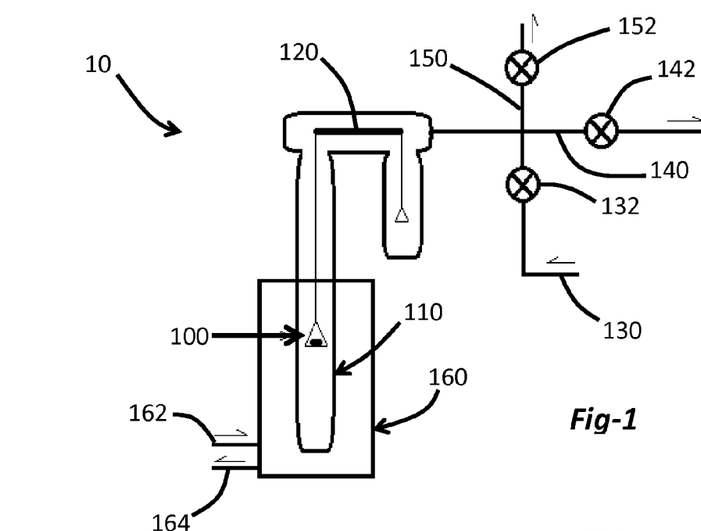
FIG. 1 is a schematic illustration of a gravimetric adsorption instrument according to an embodiment of the present invention.

Turning now to FIG. 1, an adsorption system 10 according to an embodiment of the present invention is shown. In this particular instance, the adsorption system 10 is a gravimetric adsorption system that has a sample 100 placed within an adsorption chamber 110. In addition, a microbalance 120 is provided and operable to measure the gas uptake experienced by the sample 100. The system 10 also has a probe gas inlet line 130 with a probe gas inlet valve 132. A vacuum outlet line 140 with a vacuum outlet valve 142 is also included, as well as a probe gas vent or outlet line 150 and probe gas outlet valve 152. A cooler or chiller 160 can be included with the system 10 in order to cool a probe gas from a first temperature to a lower second temperature, or in the alternative, allow cooled gas to heat up to a higher temperature. As shown in the figure, the cooler 160 can have a cooling inlet line 162 and a cooling outlet line 164.

FIG. 2 provides an illustrative flowchart for a process 20 according to an embodiment of the present invention, the process 20 provides a porosimetry instrument at step 200. For example, the porosimetry instrument can be a gravimetric gas adsorption system, a volumetric gas adsorption system of a combination thereof. In addition, a porous material sample to be characterized is provided at step 210 and an uptake target value is selected at step 220. An interval about the target value is selected at step 230 and pressure within the porosimetry instrument is adjusted in order for the uptake target value to be obtained at step 240. At step 250, the porosimetry instrument determines whether or not pressure within the system is within the target value interval for at least a predetermined amount of time ($\Delta t$), illustratively including a predetermined amount of time between 5 to 60 minutes. If not, the process returns to step 240 and pressure is adjusted until the pressure is within the target interval for at least the predetermined time. Once this has occurred, equilibrium is determined or declared to have been established and the next target value is selected at step 260. In the event that the porosimetry run is determined to complete at step 270, the run is stopped at 280; in the alternative, the process returns to step 220 and the next uptake target value is selected and steps 230-260 are completed again.

Figure 3:
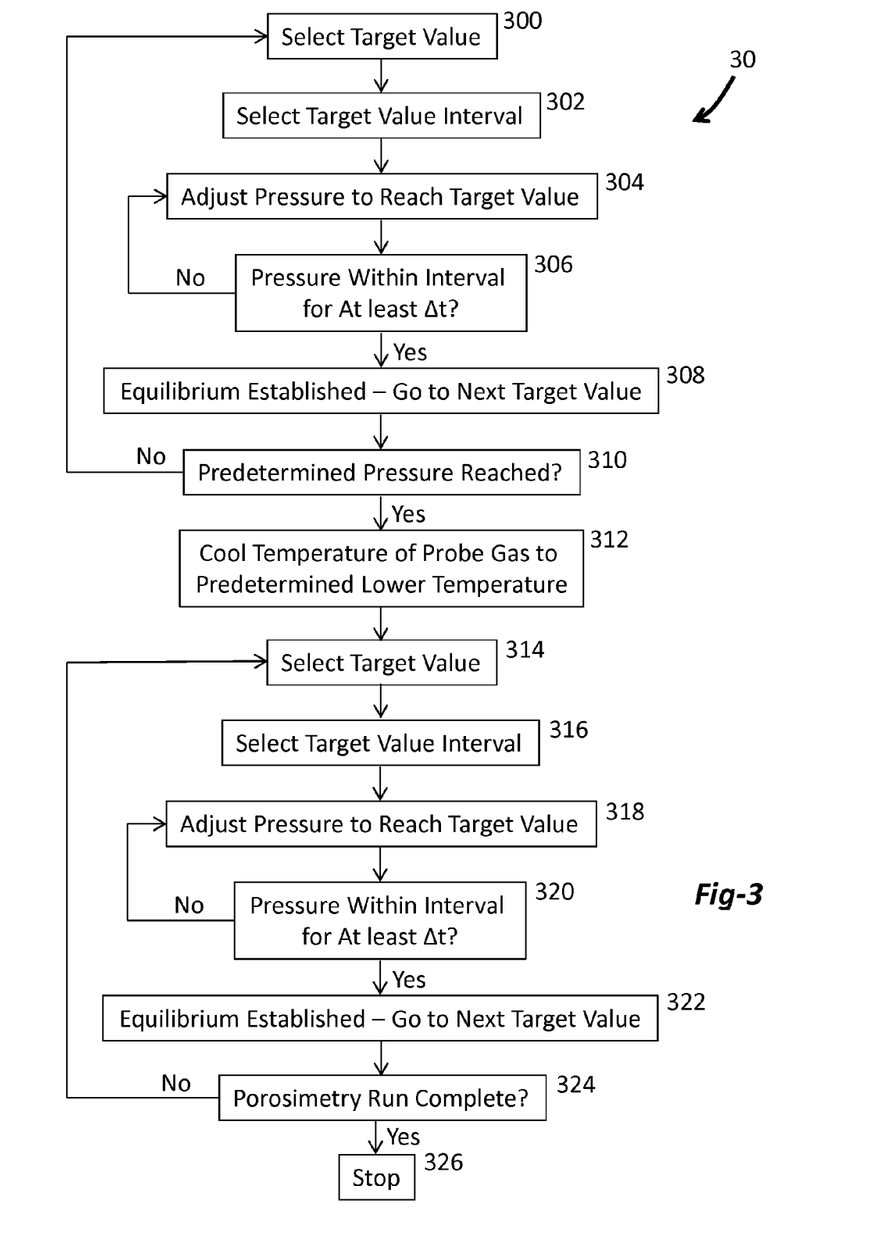
FIG. 3 is a flowchart illustrating a process according to another embodiment of the present invention.

Referring now to FIG. 3, another process according to an embodiment of the present invention is shown at reference numeral 30. The process 30 assumes that a porosimetry instrument and a porous material to be characterized have been provided and an uptake target value is selected at step 300. A target value interval is selected at step 302 and pressure within the system is adjusted in order to reach the uptake target value at step 304. In the event that the pressure within the system is maintained within the target value interval for at least a predetermined amount of time, equilibrium is determined or declared to have been established and the system goes to the next target value at step 308. However, if the pressure does not stay within the interval for the predetermined amount of time, the process returns to step 304 and pressure is adjusted until equilibrium is established.

Once equilibrium has been established, the process proceeds to step 310 and whether or not a predetermined pressure within the porosimetry instrument has been reached is determined. In the event that the predetermined pressure has not been reached, the process returns back to step 300 and steps 300-308 are completed until the predetermined pressure has been reached. After the predetermined pressure has been reached, the process proceeds to step 312 and the temperature of the probe gas is lowered to a predetermined lowered temperature. Then, the process proceeds to step 314 where an uptake target value is selected and then to step 316 where a target value interval is selected. Thereafter, pressure within the porosimetry instrument is adjusted in order to reach the uptake target value at step 318. Then, similar to step 306, whether or not the pressure is maintained within the target value interval for at least a predetermined amount of time is determined at step 320. In the event that this criteria has not been satisfied, the process returns back to step 318. Once the criteria has been satisfied, the process proceeds to step 322 in which equilibrium is determined to have been established and the process proceeds to step 324. In the event that the porosimetry run is not complete, another target value is selected at step 314 and steps 314-322 are completed again. In the event that the porosimetry run is complete, the process stops at step 326. In this manner, a single probe gas can be used to obtain one complete set of pore size distribution data ranging from micropores to mesopores to macropores.

Figure 4:
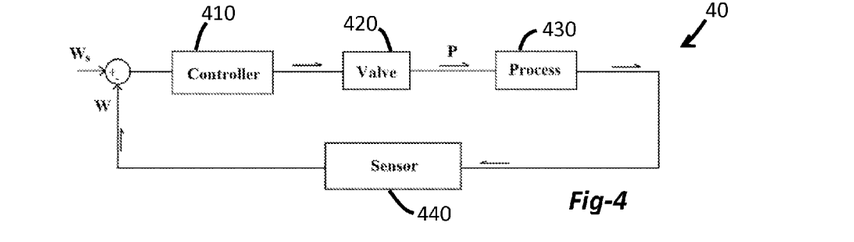
FIG. 4 is schematic illustration of a control loop for adjusting gas uptake of a sample (W) at set point ($W_s$) by manipulating pressure (P)

Not being bound by theory, the dynamics of the net adsorption processes discussed above are used to apply control theory in order to track a desired uptake value. Furthermore, and to simplify further, the adsorption kinetics are linearized to the form of an asymptotic first order transfer function:

$$\frac{W(s)}{P(s)} = \frac{K_p}{\tau_p s + 1} \quad (3)$$

where $W(s)$ is the gas uptake, $P(s)$ is the pressure, $K_p$ is the gain of the adsorption process, $\tau_p$ is the adsorption time constant and s is the Laplace domain parameter [24]. Control of an idealized adsorption system described by Equation (3) is trivial. However, in a real adsorption system there are other dynamic terms that make the overall system more complicated and the main components of a control loop 40 around such an adsorption system are illustratively shown in FIG. 4. In particular, the control loop 40 includes a process 430, e.g. an adsorption chamber, a controller 410, one or more control valves 420 and a pressure sensor 440.

The pressure of such a system is limited within the range imposed by the instrument design, which is typically chosen to operate between ultrahigh vacuum and atmosphere. At very low pressures, the feed dynamics are significantly faster than the vacuum dynamics, whereas at high pressures, the feed dynamics are slow compared to the vacuum dynamics. It is appreciated that the valve dynamics can be accounted for using linear first order transfer function.

Figure 5A:
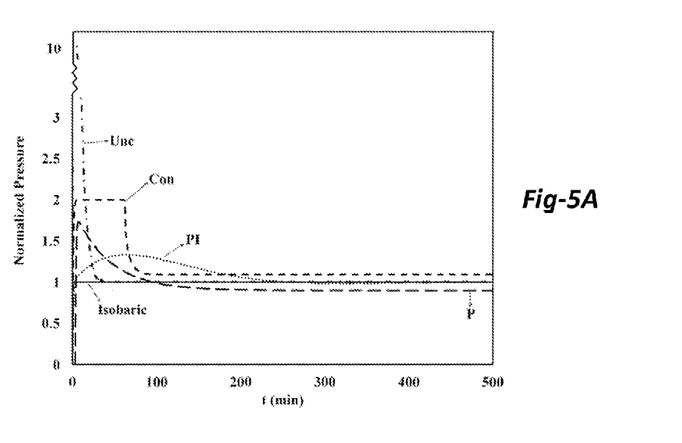
FIG. 5A is a plot illustrating simulated pressure under different control strategies: No controller (Isobaric); Proportional Controller (P); Proportional-Integral Controller (PI); Unconstrained accelerated (Unc); and Constrained accelerated (Con)
Figure 5B:
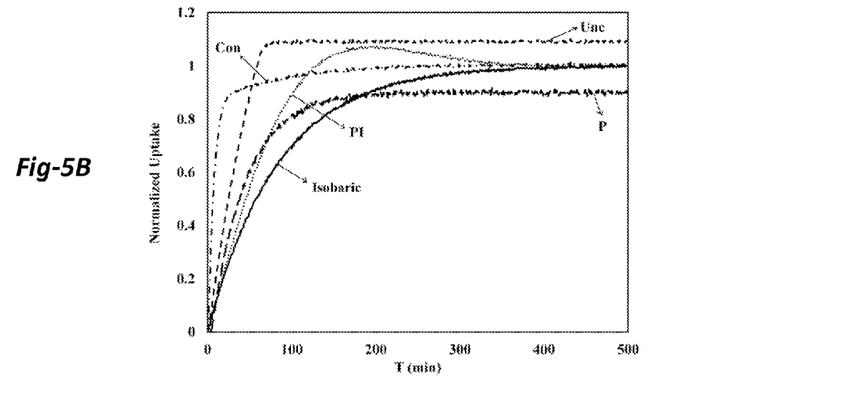
FIG. 5B is a plot illustrating simulated uptake profiles under different control strategies: No controller (Isobaric); Proportional Controller (P); Proportional-Integral Controller (PI); Unconstrained accelerated (Unc); and Constrained accelerated (Con)

Referring to FIGS. 5A and 5B, the effect of pressure variation on normalized gas uptake for the hypothetical system is shown. Pure proportional controllers suffer from the offset in the target value and an integrator can be added to the control system to remove the offset. However, addition of an integrator can introduce oscillations to the pressure and normalized uptake changes. As discussed above, oscillations in normalized gas uptake brought on by fluctuations in the mass adsorbed can introduce measurement errors due to the possible adsorption hysteresis. Along with offset and hysteresis, measurement noise can be another problem that needs to be addressed.

It is appreciated that heretofore treatment of such issues used additional filters. However, by introducing a filter, the genuine dynamics of the adsorption process are masked, thereby affecting the evaluation of the equilibrium condition. Therefore, instead of targeting the controller to a single equilibrium uptake value, a narrow interval around a target value is selected, with the magnitude of the interval comparable to the amplitude of the noise in that region. Thus within a certain amount of time, the gas uptake remains within that interval, and the process is considered to be equilibrated. By defining a target interval instead of a target value, the effect of noise on the stability of the control loop is diminished.

Considering that the valves operate in an on/off manner (solenoid valves), the time interval over which they are open determines the amount of gas injected into or removed from the adsorption system. In other words, the actions of the controller defines a series of pulses, where each pulse is composed of a time interval in which a valve is open, followed by another time interval in which the valve is closed. In this manner, the frequency of opening a valve mimics the gain of a proportional controller. Furthermore, as long as the current total sample mass (adsorbent and adsorbate) is in the target interval, the controller is off, and once the uptake hits a lower or upper boundary, the controller acts accordingly to keep the uptake within the target interval. It is appreciated that with the design of a typical instrument and its slowness of physisorption dynamics, the current uptake will not significantly deviate from the target interval, and the gain of the controller is assumed to be constant throughout the entire adsorption process.

Using such a controller on a hypothetical adsorption system, and due to the change in the definition of the control objective (from target point to target interval), operating the controller in a more aggressive manner without any stability issues can be simulated as illustrated in FIGS. 5A and 5B for the unconstrained (Unc) control case. In addition, the results show adsorption uptake is significantly faster and the controller action exceeds its normal operating point by a factor of ten. For example, applying this action to a real adsorption system operating around 100 Torr would result in the pressure being raised to approximately 1000 Torr. It is appreciated that such aggressive action is beyond the capabilities of a real adsorption system. Therefore, a limit to pressure variations is defined, e.g. a limit value defined as twice the target equilibrium pressure as illustrated in FIG. 5A by the constrained (Con) curve.

As observed by the Con curve, the initial rise is slower than for the Unc case, however the system reaches the final equilibrium point at slightly shorter overall time. This can be attributed to the slow nature of the adsorption process. As such, controller parameters that can speed up the rate of attainment of the final equilibrium step can be obtained, but only at a cost of even more aggressive changes of pressure, in some cases beyond the scope of operation. Since the constrained accelerated control approach could be used for a sub-atmospheric adsorption instrument, this approach was applied to a porosimetry technique in order to determine its effectiveness as an accelerated analysis method.

From a practical point of view, fast adsorption and accurate measurements that can be done close to room temperature and below atmospheric pressures are desirable. In this respect, a relatively high boiling point of an adsorbate molecule can be helpful to increase measurement temperatures. Also, in porosimetry studies the adsorption isotherms are collected as functions of relative pressure and obtaining a certain relative pressure and the absolute pressure of the system allows for varying the adsorption temperature. It is appreciated that this is helpful when high resolution data in the micropore region is collected.

Referring to Table 1 below, a comparison of the saturation pressure of $CO_2$, $N_2$ and MeCl at different temperatures is shown. For each gas, and as expected, the variation of saturation pressures with temperature is dramatic. Also, since the boiling point of $N_2$ is too low, any proposed change in the adsorption temperature is not practical. However, when compared to $N_2$, $CO_2$ shows great improvement since the normal boiling point is closer to room temperature. Still, even a slight change in the adsorption temperature dramatically increases the saturation pressure of $CO_2$. As such, $CO_2$ is useful for micropore characterization at sub-atmospheric, absolute pressures up to the relative pressure of ~0.04.

TABLE 1

| Probe Molecule | Corresponding Relative Pressure (P/P$_0$) at 1 bar (P$_0$ = 1)[1] | | | | | | Magnetic Susceptibility[2] (cm$^3$) (10$^{29}$) | Polarizability[2] (cm$^3$) (10$^{24}$) | Kinetic Diameter (Å)[1] |
|---|---|---|---|---|---|---|---|---|---|
| N$_2$ | 1 | (77 K) | 0.26 | (90 K) | 0.04 | (120 K) | 2 | 1.26 | 3.4 |
| CO$_2$ | 1 | (216 K) | 0.096 | (233 K) | 0.026 | (273 K) | 3.5 | 0.6 | 3.3 |
| MeCl | 1 | (249 K) | 0.38 | (273 K) | 0.15 | (303 K) | 5.31 | 4.53 | 4.18 |

[1]from Reid et al [26]
[2]from CRC Handbook [27, 28]

Compared to N$_2$ and CO$_2$, MeCl has the highest boiling point and raising the temperature even up to 303 K only increases the saturation pressure to ~7 bar. Thus similar to CO$_2$ adsorption, such a high saturation pressure is practically useful in porosimetry since the resolution of acquired data can be increased at low relative pressures.

Figure 6:
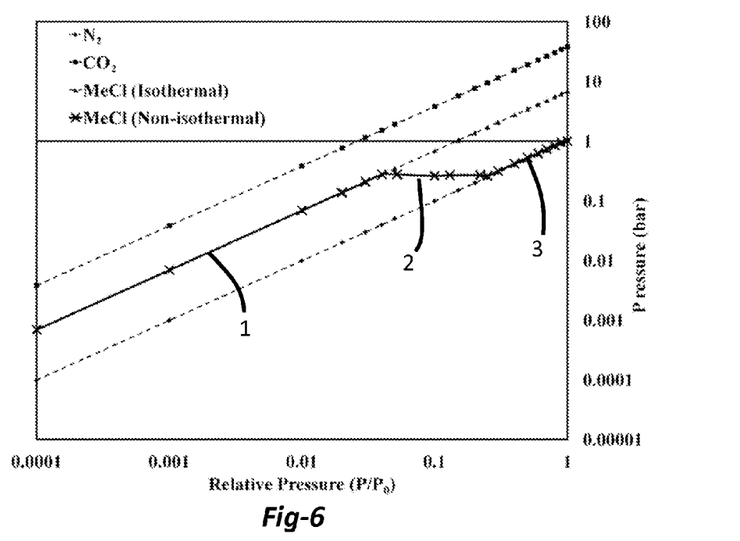
FIG. 6 is a graphical plot illustrating variations of absolute pressure versus relative pressure for $N_2$, $CO_2$ and MeCl adsorption at 77 K, 273 K and 249-303 K, respectively.

Turning now to FIG. 6, an improvement in adsorption data resolution is shown via a comparison of N2, CO2 and MeCl at 77K, 273K and 303-249K, respectively. In particular, the N$_2$ adsorption data shows a maximum N$_2$ adsorption pressure is readily limited to 1 bar, but at the cost of adsorption measurements being done at cryogenic temperatures where kinetics are slow. Moreover, extremely low absolute pressures are required to characterize micropores at relative pressures below 0.05 suggesting that ultrahigh vacuum systems are necessary. With CO$_2$ at 273 K, and considering the absolute pressure versus relative pressure profile, micropore regions can be characterized, however very high pressures would still be required to cover the whole relative pressure range—which exceeds the typical 1 bar limit for the absolute pressure in such an instrument.

In contrast, the pressure profile of MeCl at 303 K falls between the profiles of N$_2$ and CO$_2$. In addition, MeCl is similar to CO$_2$ in that it does not require ultrahigh vacuum for the measurements in micropore region and it also does not require cryogenic temperatures.

Figure 7:
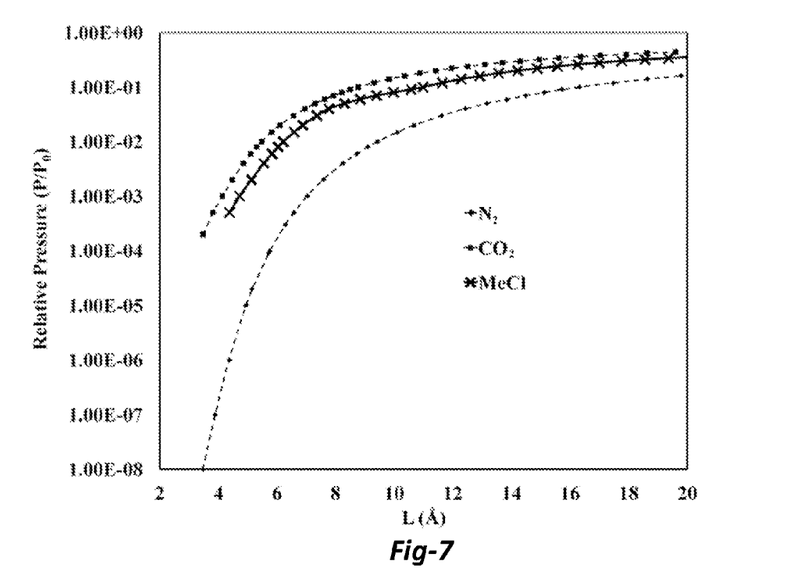
FIG. 7 is graphical plot illustrating relative pressure versus effective pore size calculated by the HK model for $N_2$, $CO_2$ and MeCl at 77, 273 and 303 K, respectively.

FIG. 7 provides an overview of the effect of adsorption pressure on the micropore size characterization with the pore size distribution profiles theoretically calculated using the HK method. It is appreciated that HK models are typically assigned for slit pores of carbon adsorbents. Also, at the temperature at which micropore characterization is conducted with MeCl (303 K), the HK model takes the following form $$RT \ln\left(\frac{P}{P_0}\right) = \frac{58060}{L - 0.758}\left[\frac{3.73 \times 10^{-3}}{(L - 0.379)^2} - \frac{1.47 \times 10^{-6}}{(L - 0.379)^9} - 0.0594\right] \quad (4)$$

where L is the pore size in Å, P is the pressure of the gas, P$_0$ is the saturation pressure at temperature T and R is the gas constant.

To detect the smallest pore size accessible by MeCl, the vacuum required for N$_2$ is ~1000 times more than for MeCl or for CO$_2$. In addition, FIG. 7 illustrates that for micropore characterization above 4 Å, MeCl is as suitable a gas adsorbate as CO$_2$. It is appreciated that in order for MeCl to cover the whole desired range of relative pressures, 7 bar pressure is required at the upper end. However, the high boiling point of MeCl allows a drop in temperature to be executed instead of raising the pressure to attain the result. For example, in order to keep absolute pressures below 1 bar the temperature only has to be reduced to 249 K and thus a non-isothermal MeCl adsorption procedure can be used to cover the entire range.

Referring back to FIG. 6, the non-isothermal MeCl adsorption procedure is composed of three sections. In the first section 1, the micropore region is characterized by adsorption measurements conducted at 303 K. In the second section 2, the pressure of the adsorption system is kept constant and temperature is reduced to the normal boiling point. And in the third section 3, the temperature hits the target value and the pressure of the adsorption system is increased towards a relative pressure of ~0.99. In this manner it is theoretically possible to determine micro and mesoporosity of any porous material with a single adsorption run near room temperature and under sub-atmospheric pressures with one adsorbate, i.e. MeCl.

In order to provide an example of the inventive process and yet not limit the scope of the invention in any way, the setup and/or results of one or more experiments are provided below.

Experiments

MeCl gas was obtained from GTS-Welco at a purity of 99.9% and was used in the experiments without further purification. ZSM-5 and faujasite (CBV-780) materials were purchased from Zeolyst and SBA-15 and MCM-48 materials were obtained from ClayTec. Polyfurfuryl alcohol (PFA)-derived microporous carbon was synthesized via a procedure explained elsewhere [1] and was notated as 'NPC'. A sample of CO$_2$ oxidized PFA-derived carbon was synthesized by heat treatment of NPC under CO$_2$ at 1173 K until a 40% burn-off was reached/obtained. This sample was notated NPC-40.

A mesoporous carbon sample was synthesized following Dai's method [2] with 1.25 grams of Phloroglucinol mixed in a solution of 1.25 F-127 dissolved in 4.26 grams of water and 4.76 grams of EtOH. After 30 minutes, 5 drops of HCl 37% were added to the solution and after 30 minutes the solution turned a light pink color. Formaldehyde (1.3 grams) was then added to the solution and the solution allowed to sit for 1 hour while being stirred by a magnetic stirrer—at which time the magnet stirrer had stopped due to the solution/polymer viscosity. Excess water and EtOH were removed from the polymer and the polymer was dried at 373 K overnight. Next, carbon was pyrolized from the polymer by heating the material at 1123 K for 3 hours in air, followed by sieving down to 75 microns. This sample was notated 'MSC'.

A carbon sample with bimodal micro and mesoporosity was synthesized by oxidizing MSC with CO$_2$ at 1173 K for 1 hour and this sample was notated 'MSC-Ox'.

The instrument used for the porosimetry measurements study was a custom-made gravimetric adsorption system equipped with a chiller operating the temperatures between −40° C. and 120° C. The instrument was facilitated by a two stage roughing pump and a turbo-pump. In addition, two pressure transducers with ranges of 0-10 and 0-1000 Torr measured gas pressure.

For each run, an appropriate amount of sample, ~150 mg, was loaded on an instrument pan, the instrument was sealed, depressurized down to 0.001 Torr and subsequently baked out to clean the surface of the adsorbent. For carbon and silica/alumina samples the degassing temperature was adjusted at 300° C. and 150° C., respectively. In addition, 6 hours of the degassing heat treatment was enough to reach a stable uptake.

After degassing, the system was cooled down to a desired temperature and the adsorption measurements were initiated. Adsorption data were collected point by point and to reach equilibrium at each data point the control system manipulated pressures to accelerate the adsorption dynamics. Measurements were conducted between 0.0001-700 Torr and the amount of gas injected into the system or pumped out of the system was controlled using two flow restrictors added to the instrument. In addition, the adsorption and desorption processes were automatized by a LabView application designed for the instrument.

The accelerated porosimetry method was applied to the carbons and aluminosilicate samples using a similar temperature program for each material. In a typical experiment, adsorption was started at 303 K and pressures below $P/P_0=0.2$. Then at a pressure of 200 Torr, the temperature was gradually reduced from 303 K to 249 K with a temperature step of ~5 K. During temperature changes, and along with the stability of the gas uptake and gas pressure, thermal equilibrium was confirmed. Optimum control parameters were obtained and observed to be a function of the specifications of the adsorption instrument, i.e. volume, feed pressure, capacity of the pumping system, and valve and nozzle sizes. The average optimum control parameters for the adsorption instrument are reported in Table 2 below.

TABLE 2

| Sample | Rise time (min) | Equilibrium time (min) | Pulse (On) | Pulse (Off) | Pressure threshold (Torr/min) | Temperature threshold (K/min) |
|---|---|---|---|---|---|---|
| Carbon | 30 | 15 | 5 | 1 | 0.05 | 0.1 |
| Alumino-silicate | 10 | 10 | 1 | 1 | 0.05 | 0.1 |

The adsorption measurements in Table 2 illustrate adsorption rates on the aluminosilicate samples were significantly faster than on the carbon samples and the more conservative parameters for adsorption on the carbon samples were chosen for additional measurements discussed below unless otherwise noted. In addition, a fifteen minute initial rise under constant pressure was sufficient to reach an acceptable amount of gas uptake that was distant enough from gas uptake at the previous data point for most micro and mesoporous carbon samples. Once a rise time was established, a narrow interval around a current value of gas uptake was defined and using an on/off control mode that executed a set of vacuum and feed pulses, the pressure of the system was manipulated to keep adsorption uptake within a target interval.

Equilibrium times were defined, i.e. times at which to check the equilibrium of the adsorption system. For carbon and aluminosilicate samples, 15 and 10 minutes were set, respectively. If the pressure did not cross interval boundaries during or within a given equilibrium time, the system was assumed to be at equilibrium. Also, temperature and pressure variations were monitored to ensure variations were less than a predefined tolerance.

During the equilibrium time, the pressure of the system was controlled by pressure impulses. For example, if the uptake crossed the upper boundary during carbon sample runs, the vacuum valve was opened for 3 seconds and then closed for 1 second, and continued until the uptake returned back to the upper boundary. In the same manner, if the uptake crossed the lower boundary, the feed valve was opened for 3 second and then closed for 1 second, and continued until the uptake returned back to the upper boundary. This ratio between On-time and Off-time modes was the gain of the controller and thus the gain for the carbon samples was three while the gain for the aluminosilicate sample was one.

Textural properties of carbon and aluminosilicate samples obtained using the inventive process are summarized in Table 3 below. The properties measured by MeCl were obtained by the accelerated algorithm and compared to the data reported in the literature. The micro (HK, SF) and mesopore (modified Kelvin) models were applied to the adsorption data of each sample to determine the pore size distribution profiles along with the total pore volume at the highest measurement pressure $\sim P/P_0=0.95$. It is appreciated that the SF requires the assumption of line average or area average of the interactive forces inside a pore, due to the curvature of the cylindrical pores. Assuming an area average an infinite series as follows can be written:

$$RT \ln\left(\frac{P}{P_0}\right) = 18167 \quad (5)$$

$$\sum_{k=0}^{\infty}\left[\frac{1}{k+1}\left(1 - \frac{0.758}{D}\right)^{2k} \times \left\{\frac{21}{35}\alpha_k\left(\frac{0.758}{D}\right)^{10} - \beta_k\left(\frac{0.758}{D}\right)^4\right\}\right]$$

where D is the pore diameter in Å. Also, the expansion coefficients can be expressed as:

$$\alpha_k = \left(\frac{-4.5-k}{k}\right)^2 \alpha_{k-1} \quad (6)$$

$$\beta_k = \left(\frac{-1.5-k}{k}\right)^2 \beta_{k-1} \quad (7)$$

with $\alpha_0$ and $\beta_0$ equal to 1. By evaluating equation 5 at different pressures, the first 12 terms of the expansion provide an accuracy of ≤0.001%.

Characterization of the carbon samples with MeCl using the accelerated method showed good agreement with standard $N_2$ adsorption at 77 K. In addition, the small differences between the pore volumes and mean pore sizes suggests that even for purely microporous carbon (NPC) with a mean pore size of 5 Å, the overall accessibility to the pores for $N_2$ and MeCl are similar.

TABLE 3

| | | Pore Volume (cc/g) | | | Mean Pore Size (Å) | | |
|---|---|---|---|---|---|---|---|
| Sample | Reference | MeCl | Ref | ΔV | MeCl | Ref | ΔL |
| ZSM-5 | 43, 45 | 0.18 | 0.21 | 0.03 | 5.6 | 5.1 * 5.7 | 0.2 |
| CBV-780 | 4, 6, 11, 12, 13 | 0.46 | 0.45 | 0.01 | 9 | 10 | 1 |
| MCM-48 | 8, 9, 4, 10 | 0.8 | 0.85 | 0.05 | 20 | 22 | 2 |
| SBA-15 | 7, 14 | 1.09 | 1.1 | 0.01 | 69 | 70 | 1 |
| NPC | 1 | .18 | 0.19 | 0.01 | 5.1 | 5.2 | 0.1 |
| NPC-40 | 1 | 0.62 | 0.59 | 0.03 | 6.2 | 6.4 | 0.2 |
| MSC | 2, 3 | 0.64 | 0.66 | 0.02 | 87 | 81 | 6 |
| MSC-Ox | | 0.87 cc/g | | | Mean Micropore 6 Å, mean mesopore 106 Å | | |

The pore size of aluminosilicate materials can be accurately evaluated by X-ray diffraction, as reported in the literature or for commercial samples [4-15]. As such, two microporous aluminosilicate samples (ZSM-5, CBV-780) and two mesoporous aluminosilicate samples (MCM-48, SBA-15) were chosen to evaluate the accuracy of the accelerated method. With the ZSM-5 sample, the size of cage and pore mouth were reported as 5.6 Å and 5.3 Å [4], respectively, whereas the value calculated with MeCl adsorption was 5.6 Å. With CBV-780, the measured mean pore size was approximately 9 Å, fairly close to the pore sizes reported in the range of 7-12 Å [4, 6]. Therefore, MeCl adsorption is viable for characterization of microporous aluminosilicate structures.

In a similar set of experiments, the mean pore sizes of MCM-48 and SBA-15 mesoporous samples measured by accelerated MeCl adsorption were nearly 20 nm and 69 nm, which is general agreement with the reference values of 22 and 70 nm, respectively [7-10].

Figure 8A:
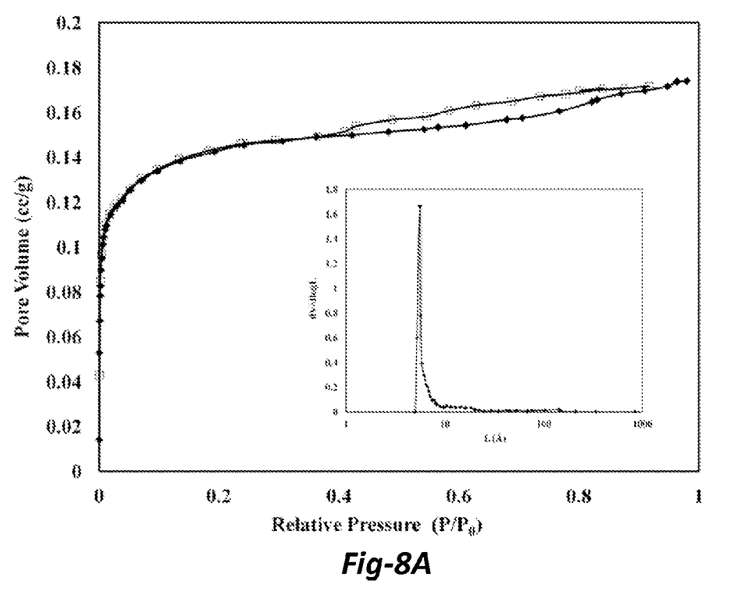
FIG. 8A is graphical plot illustrating adsorption-desorption profiles of MeCl on a ZSM-5 sample and measured under non-isothermal conditions using the accelerated method (hereafter "accelerated measurement(s)" or "accelerated method(s)") according to an embodiment of the present invention with the inset showing a pore size distribution profile calculated from the adsorption branch.
Figure 8B:
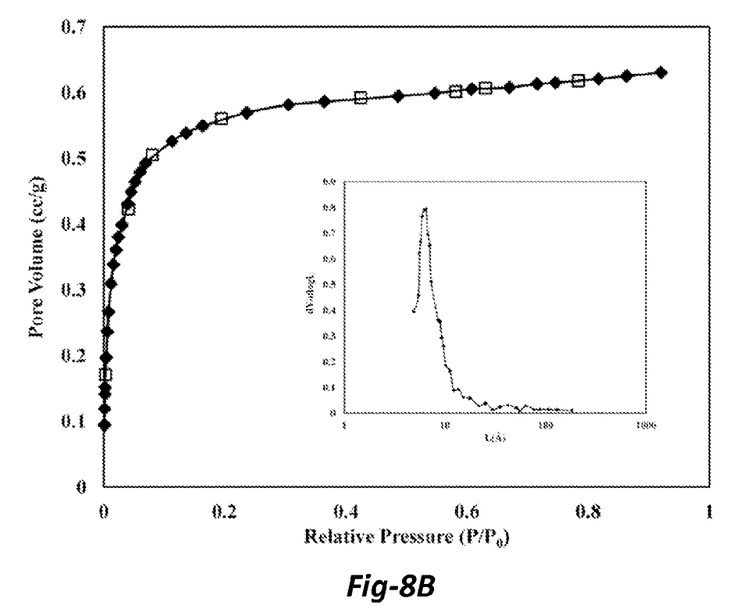
FIG. 8B is graphical plot illustrating adsorption-desorption profiles of MeCl on a NPC-40 sample and measured under non-isothermal conditions using the accelerated method (hereafter "accelerated measurement(s)" or "accelerated method(s)") according to an embodiment of the present invention with the inset showing a pore size distribution profile calculated from the adsorption branch.

The MeCl molecule has a strong dipole moment of 1.87 D that can contribute to electrostatic interactions with a surface and can complicate pore size analysis by selective adsorption on the surfaces of some adsorbents, especially aluminosilicate samples. However, such effects were not observed. FIG. 8A shows the adsorption-desorption profile for ZSM-5 along with a calculated pore size distribution. Although a sample is purely microporous because of the presence of some constrictions in the framework, a cavitation point was observed which has also been reported for $N_2$ adsorption [3]. In addition, at pressure below $P/P_0=0.05$ the adsorption-desorption isotherms overlay each other, thereby suggesting that MeCl is not chemically interacting with the surface. FIG. 8B shows MeCl adsorption-desorption profiles on the NPC-40 sample. In this case no TSE point was observed. Since $CO_2$ oxidation starts etching the surface from the outside, eventually it forms a porous network with the least amount of constrictions.

Figure 9A:
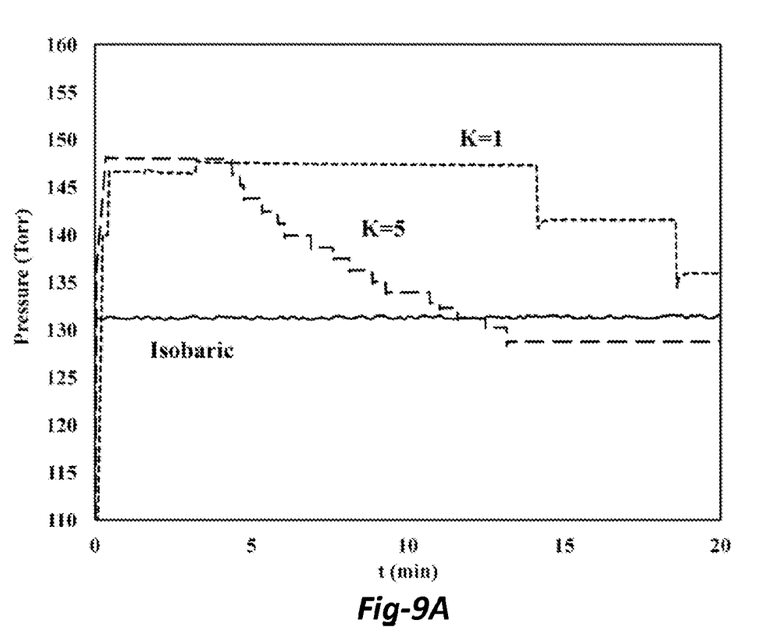
FIG. 9A is a graphical plot illustrating pressure variations measured for isobaric and accelerated measurements with K=1 and K=5.
Figure 9B:
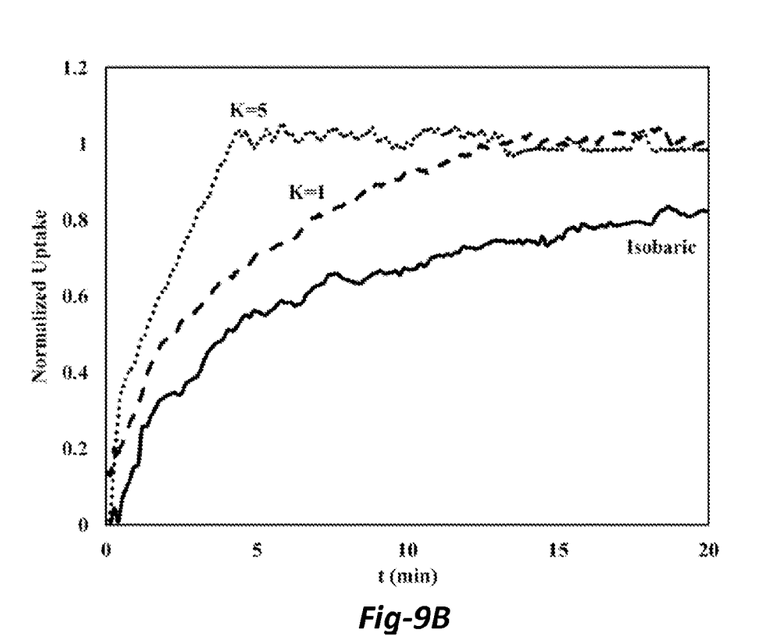
FIG. 9B is a graphical plot illustrating normalized gas uptake measured for isobaric and accelerated measurements with K=1 and K=5.

FIGS. 9A and 9B illustrate the effect of the gain of the controller (K) on the adsorption dynamics of MeCl on NPC. The curves for K=1 and K=5 represent a pressure change of ~100 Torr to ~130 Torr at 303 K. The rise time and equilibrium time were chosen to be 5 and 15 minutes respectively. The figure shows the first 20 minutes of pressure and weight measurements of an equilibrium time. When the controller gain approached zero, the system dynamics were as slow as the genuine dynamics of the adsorption process during isobaric measurement. As the controller gain became larger the speed at which the adsorption system attains equilibrium became faster and only for very large values of the gain did the adsorption system show oscillations.

Figure 10A:
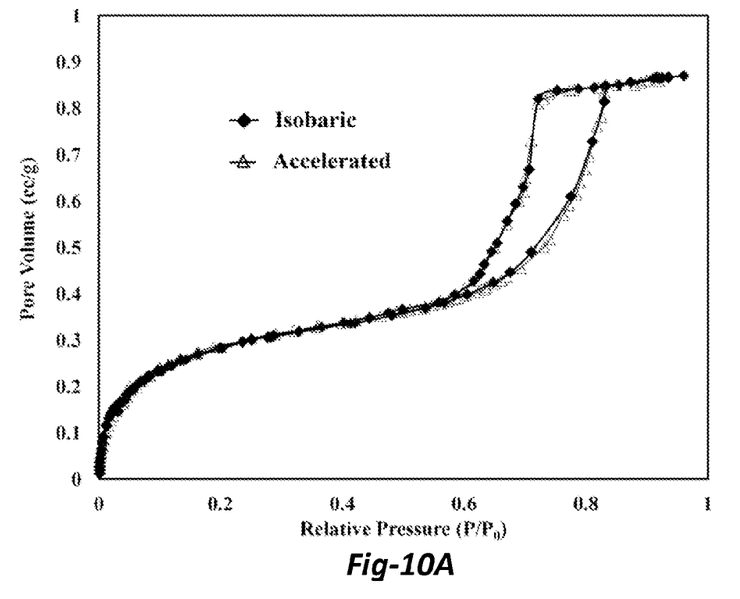
FIG. 10A is a graphical plot illustrating adsorption-desorption profiles of a MSC-Ox sample and measured via isobaric and accelerated methods.
Figure 10B:
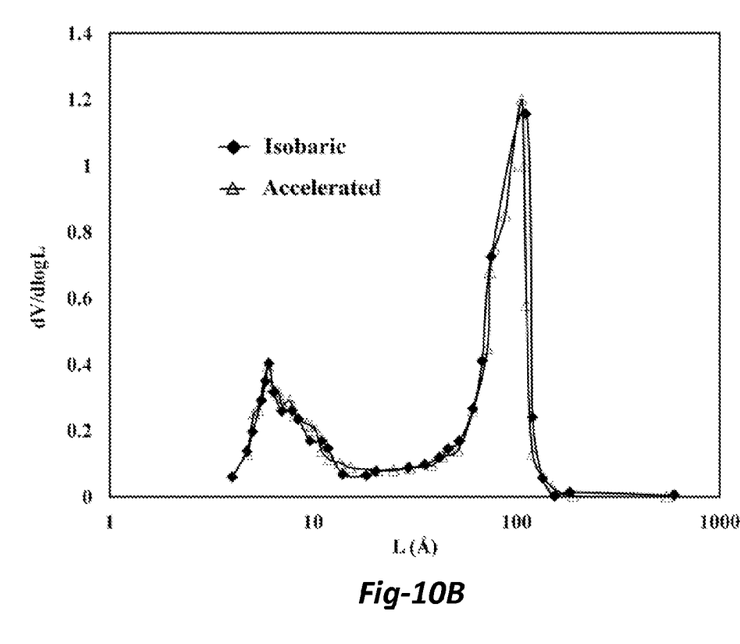
FIG. 10B is a graphical plot illustrating pore size distribution of a MSC-Ox sample and measured via isobaric and accelerated methods.

The MeCl isobaric and accelerated measurements were compared on the bimodal micro-meso porous carbon (MSC-Ox). The controller parameters suggested in Table 2 were conservative and for some samples more aggressive measurements were taken within a shorter period of time. For such aggressive measurements, an increase in the controller gain to 5 was taken for the micropore region. Moreover, the rise time and equilibrium time were adjusted as 15 min and 5 min, respectively. FIGS. 10A and 10B compare the isobaric and the aggressive accelerated MeCl adsorption measurements for the sample with the adsorption-desorption uptakes as well as their corresponding pore size distribution profiles in good agreement. However, because of the speed issue with the isobaric method only 40 data points were collected whereas with the accelerated method over 100 data points were collected. On average, equilibration times at each data point with the isobaric versus accelerated methods were 75 min and 20 min respectively, showing an improvement factor of approximately 4.

Figure 11A:
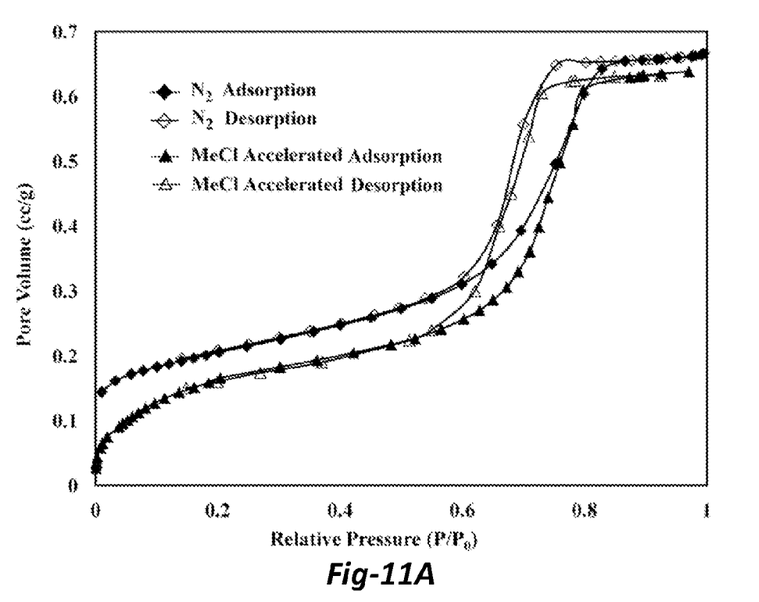
FIG. 11A is a graphical plot illustrating adsorption-desorption profiles of a MSC sample and measured by $N_2$ adsorption at 77 K and MeCl via the accelerated methods.
Figure 11B:
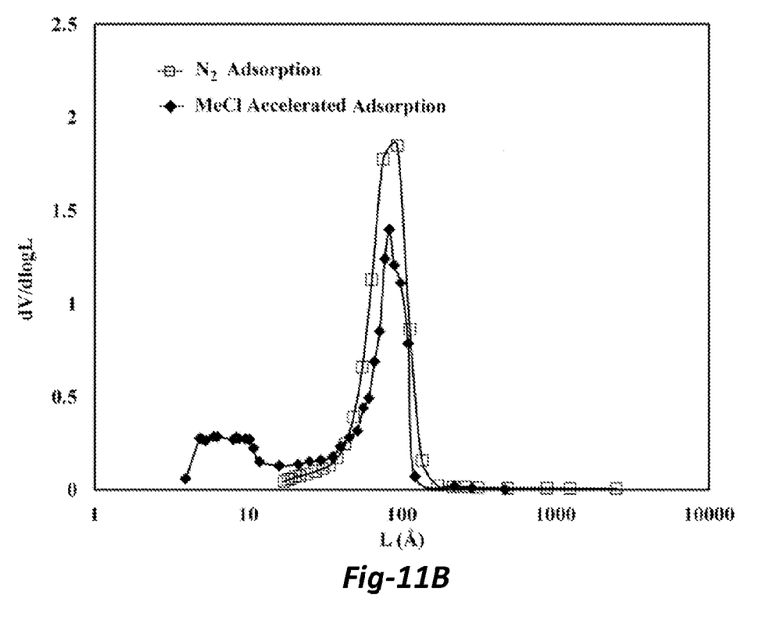
FIG. 11B is a graphical plot illustrating pore size distribution of a MSC sample and measured by $N_2$ adsorption at 77 K and MeCl via the accelerated methods.

Turning now to FIGS. 11A and 11B, MeCl uptake profiles measured via accelerated MeCl adsorption versus $N_2$ adsorption isotherms at 77 K for MSC, the purely mesoporous carbon sample, are shown. Due to the different probes used in the measurements as well as the non-isothermal nature of the MeCl adsorption measurements, the uptake profiles are different from each other. However, the textural properties and pore size distribution profiles measured by both probes in the mesopore region are in good agreement. This suggests that although the uptake profiles are different, choosing appropriate models removes discrepancies resulting in similar pore size distribution profiles. However, in the micropore region, ($P/P_0<0.05$), the $N_2$ adsorption data show a sudden rise suggesting the presence of micropores in the carbon structure that are not detected by MeCl. For $N_2$, this rise is also observed for other mesoporous materials especially in aluminosilicates and it has been attributed to anomalous adsorption at the corrugations on the pore walls, a process that mimics adsorption in the micropores [5, 6].

Figure 12A:
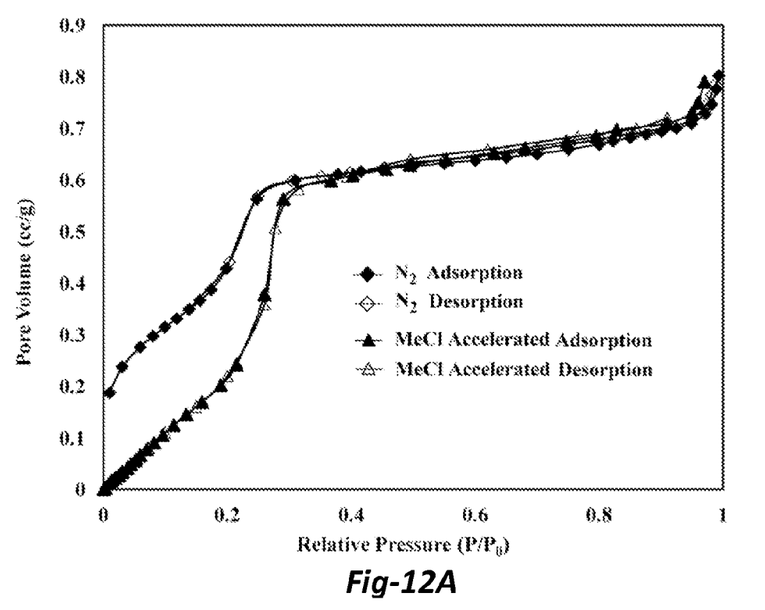
FIG. 12A is a graphical plot illustrating adsorption-desorption profiles of a MCM-48 sample and measured by $N_2$ adsorption at 77 K and MeCl via the accelerated method.
Figure 12B:
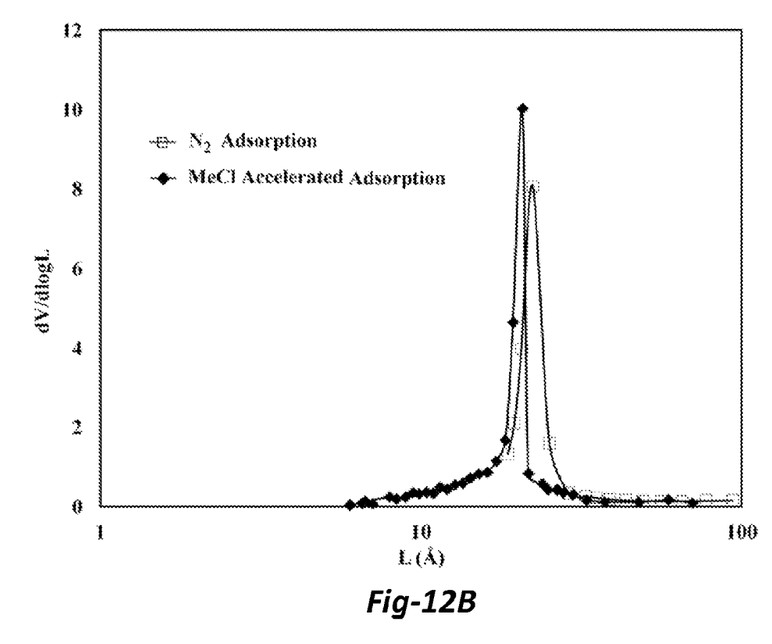
FIG. 12B is a graphical plot illustrating pore size distribution of a MCM-48 sample and measured by $N_2$ adsorption at 77 K and MeCl via the accelerated method.

A drastic difference was observed between the adsorption of MeCl on MCM-48 via the accelerated method and $N_2$ adsorption at 77 K as depicted in FIGS. 12A and 12B. In the micropore region the measured adsorption profiles are completely different but they are similar in the mesopore regions. Pore size based on $N_2$ was calculated by the modified Kelvin method whereas for the MeCl data the micropore size was calculated using SF model and the mesopore size was evaluated by the modified Kelvin method. Here again, based on what is known of the structure of MCM-48, the MeCl method did not detect any microporosity, whereas the $N_2$ isotherm shows a jump at very low pressures.

It is appreciated that BJH, or KJS modifications of the Kelvin model are the common methods to evaluate mesopore size distribution. The Kelvin equation is defined as:

$$r_c = \frac{-2\gamma V \cos\theta}{RT\ln\left(\frac{P}{P_0}\right)} \tag{8}$$

where $r_c$ is the core radius of a pore, $\gamma$ is surface tension, V is specific volume and $\theta$ is contact angle. In mesopores it is common to assume the contact angle, $\theta$, to be zero and the pore radius can be calculated from the core radius as:

$$r_p = r_c + t \tag{9}$$

where t as the thickness of the multilayer adsorbed on the pore wall. Harkins and Jura proposed an empirical equation to estimate thickness of the adsorbed layer for $N_2$ adsorption at 77 K. By using the adsorption energetics data reported for the adsorption of MeCl and comparing them with $N_2$ adsorption data, the Harkins-Jura correlations were used to calculate the thickness of MeCl adsorbed layer using the relation:

$$t = \sqrt{\frac{13.99}{0.034 - \log\left(\frac{P}{P_0}\right)}} \tag{10}$$

Also the following correlation has been shown as a simple but very accurate method to calculate pore size from core size:

$$r_p = \frac{r_0}{0.72} + 7.2 \quad (11)$$

The above correlations were derived for $N_2$ adsorption data at 77 K. However these expressions were used for the MeCl adsorption and estimated the validity of the assumption by evaluating the Kelvin model in the following form:

$$r_c = \frac{-K}{\ln\left(\frac{P}{P_0}\right)} \quad (12)$$

where K is a constant which for a molecule only varies by temperature. Evolution of this model for $N_2$ at 77 K and MeCl at 249 K by using corresponding molar volume and surface tensions resulted in K=9.62 for both molecules and it was assumed that the bulk behavior of both molecules was similar. Therefore, the correlations derived for $N_2$ were deemed to be applicable for MeCl with comparison of the pore size distributions measured using the accelerated method disclosed herein with data reported in the literature confirms the accuracy of the assumption.

The aggressive accelerated measurements were also executed by changing the controller parameters to a 5 minute rise, 5 minutes in equilibrium and a controller gain of 5 for the MCM-48 and SBA-15 samples as well. For these silica samples the adsorption measurements were faster by a factor of ~5.

The above described illustrations, embodiments, and/or examples are for illustrative examples only and are not meant to limit the scope of the invention. Changes, modifications, and the like will be apparent to those skilled in the art. As such, the scope of the invention is defined by the claims and all equivalents thereof.

REFERENCES (1) Burket C. L.; Rajagopalan R.; Marencic A. P.; Dronvajjala K.; Foley H. C. Genesis of porosity in polyfurfuryl alcohol derived nanoporous carbon. *Carbon.* 2006, 44, 2957-2963
(2) Liang C.; Dai S. Synthesis of Mesoporous Carbon Materials via Enhanced Hydrogen-Bonding Interaction. *J. Am. Chem. Soc.,* 2006, 128 (16), 5316-5317
(3) www.zeolyst.com
(4) www.claytecinc.com
(5) Du X., Wu E. Porosity of microporous zeolites A, X and ZSM-5 studied by small angle X-ray scattering and nitrogen adsorption. *Journal of Physics and Chemistry of Solids* 2007, 68, 1692-1699
(6) Htun M. M. H.; Htay M. M.; Lwin M. Z. Preparation of Zeolite (NaX, Faujasite) from Pure Silica and Alumina Sources. *International Conference on Chemical Processes and Environmental issues (ICCEEI '2012) Singapore.* 2012, Jul. 15-16
(7) Kruk M.; Jaroniec M.; Ko C. H.; Ryoo R. Characterization of the Porous Structure of SBA-15. *Chem. Mater.* 2000, 12, 1961-1968
(8) Ryoo R.; Joo S. H.; Kim J. M. Energetically Favored Formation of MCM-48 from Cationic-Neutral Surfactant Mixtures. *J. Phys. Chem. B.* 1999, 103, 7435-7440
(9) Guan L. C.; Nur H.; Endud S. Bimodal Pore Size Mesoporous MCM-48 Prepared by Post-Synthesis Alumination. *Journal of Physical Science.* 2006, 17(1), 65-75
(10) Solovyov L. A.; Belousov O. V.; Dinnebier R. E.; Shmakov A. N.; Kirik S. D. X-ray Diffraction Structure Analysis of MCM-48 Mesoporous Silica. *J. Phys. Chem. B,* 2005, 109 (8), 3233-3237
(11) Macko T.; Denayer J. F.; Pasch H.; Pan L., Li J., Raphael A. Raphael Adsorption of Polypropylene and Polyethylene on Liquid Chromatographic Column Packings. *Chromatographia.* 2004, 59, 461-467
(12) Janssen A. H.; Koster A. J.; de Jong K. P. Three-Dimensional Transmission Electron Microscopic Observations of Mesopores in Dealuminated Zeolite Y. *Angew. Chem.* 2001, 113(6), 1136-1138
(13) Wang X.; Zhang Q.; Yang S.; Wang Y. Iron-Catalyzed Propylene Epoxidation by Nitrous Oxide Studies on the Effects of Alkali Metal Salts. *J. Phys. Chem. B* 2005, 109, 23500-23508
(14) Thommes M.; Kohn R.; Froba M. Sorption and pore condensation behavior of pure fluids in mesoporous MCM-48 silica, MCM-41 silica, SBA-15 silica and controlled pore glass at temperatures above and below the bulk triple point. *Applied Surface Science.* 2002, 196, 239-249
(15) Ustinov E. A.; Do D. D.; Jaroniec M. Adsorption of argon and nitrogen in cylindrical pores of MCM-41 materials: application of density functional theory. *Applied Surface Science,* 2005, 252, 1013-1028

The invention claimed is:

1. A porosimetry process comprising:
providing an adsorption system having an adsorption chamber and a probe gas at a first temperature;
providing a porous material and placing the porous material within the adsorption chamber;
executing a porosimetry run on the porous material, the porosimetry run including:
(a) selecting an uptake target value;
(b) selecting a target interval bounding the uptake target value;
(c) adjusting pressure within the adsorption chamber in order for the porous sample to reach the uptake target value;
(d) adjusting pressure within the adsorption chamber until the pressure within the adsorption chamber is within the target interval for a predetermined amount of time; and
(e) repeating steps (a)-(d) until the porosimetry run is complete.

2. The porosimetry process of claim 1, further including:
determining if a predetermined pressure has been reached within the adsorption chamber after step (d);
cooling the probe gas from the first temperature to a predetermined lower second temperature if the predetermined pressure has been reached; and
repeating steps (a)-(d) using the probe gas at the second temperature until the porosimetry run is complete, the completed porosimetry run operable to obtain one complete set of pore size distribution data ranging from micropores to mesopores to macropores.

3. The porosimetry process of claim 2, wherein the probe gas is MeCl.

4. The porosimetry process of claim 3, further including the adsorption system having a cooler operable to cool the probe gas from the first temperature to the second temperature.

5. The porosimetry process of claim 4, wherein the probe gas is cooled isobarically.

6. The porosimetry process of claim 5, wherein the porosimetry run is a single porosimetry run from 0.001 to 700 bar.

7. The porosimetry process of claim 5, wherein the porosimetry run is a single porosimetry run from 0.005 to 700 bar.

8. The porosimetry process of claim 5, wherein the porosimetry run is a single porosimetry run from 0.01 to 700 bar.

9. The porosimetry process of claim 1, wherein the target interval is less than or equal to +/−20% of the uptake target value.

10. The porosimetry process of claim 9, wherein the target interval is less than or equal to +/−15% of the uptake target value.

11. The porosimetry process of claim 10, wherein the target interval is less than or equal to +/−10% of the uptake target value.

12. The porosimetry process of claim 1, further including the adsorption system having a probe gas inlet valve and a probe gas outlet valve and adjusting the pressure within the adsorption chamber is performed by the probe gas inlet valve or the probe gas outlet valve being in an open position.

13. The porosimetry process of claim 12, wherein the probe gas inlet valve and the probe gas outlet valve are both in the closed position when the pressure within the adsorption chamber is within the target interval.

14. The porosimetry process of claim 13, wherein the probe gas inlet valve is opened when the pressure in the adsorption chamber drops below the target interval.

15. The porosimetry process of claim 13, wherein the probe gas outlet valve is opened when the pressure in the adsorption chamber rises above the target interval.

16. A porosimetry process comprising:
   providing a gravimetric adsorption system having an adsorption chamber, a probe gas at a first temperature, a probe gas inlet valve and a probe gas outlet valve;
   providing a porous material and placing the porous material within the adsorption chamber;
   executing a porosimetry run on the porous material, the porosimetry run including:
   (a) evacuating the adsorption chamber to a predetermined vacuum pressure;
   (b) selecting a probe gas uptake pressure target value;
   (c) selecting a target interval bounding the probe gas uptake pressure target value, the target interval being at least +/−10% of the probe gas uptake pressure target value;
   (d) flowing a predetermined amount of the probe gas into the adsorption chamber in order for the adsorption chamber to reach the probe gas uptake pressure target value;
   (e) opening and closing the probe gas outlet valve and probe gas inlet valve in order to adjust the pressure within the adsorption chamber to be within the target interval for a predetermined amount of time; and
   (f) repeating steps (a)-(d) until the porosimetry run is complete.

17. The porosimetry process of claim 16, wherein the probe gas inlet valve and the probe gas outlet valve are both in a closed position when the pressure within the adsorption chamber is within the target interval.

18. The porosimetry process of claim 17, wherein the probe gas inlet valve is opened when the pressure in the adsorption chamber rises drops below the target interval.

19. The porosimetry process of claim 18, wherein the probe gas outlet valve is opened when the pressure in the adsorption chamber rises above the target interval.

20. The porosimetry process of claim 19, further including:
   determining if a predetermined pressure has been reached within the adsorption chamber after step (d);
   cooling the probe gas from the first temperature to a predetermined lower second temperature if the predetermined pressure has been reached; and
   repeating steps (a)-(d) using the probe gas at the second temperature until the porosimetry run is complete, the completed porosimetry run operable to obtain one complete set of pore size distribution data ranging from micropores to mesopores to macropores.

* * * * *